(12) United States Patent
Yu

(10) Patent No.: US 11,447,386 B2
(45) Date of Patent: Sep. 20, 2022

(54) VAPORIZATION DEVICE

(71) Applicant: KSY Technologies LLC., City of Industry, CA (US)

(72) Inventor: Carson Yu, City of Industry, CA (US)

( * ) Notice: Subject to any disclaimer, the term of this patent is extended or adjusted under 35 U.S.C. 154(b) by 127 days.

(21) Appl. No.: 16/589,147

(22) Filed: Oct. 1, 2019

(65) Prior Publication Data
US 2020/0178616 A1 Jun. 11, 2020

Related U.S. Application Data

(60) Provisional application No. 62/776,424, filed on Dec. 6, 2018.

(51) Int. Cl.
| | | |
|---|---|---|
| *A24F 11/00* | (2006.01) | |
| *B67D 7/02* | (2010.01) | |
| *A61M 11/04* | (2006.01) | |
| *G08B 21/02* | (2006.01) | |
| *G16H 20/10* | (2018.01) | |
| *G08B 3/10* | (2006.01) | |
| *G06F 3/02* | (2006.01) | |
| *G08B 6/00* | (2006.01) | |
| *G08B 5/36* | (2006.01) | |

(52) U.S. Cl.
CPC ......... *B67D 7/0288* (2013.01); *A61M 11/042* (2014.02); *G08B 21/02* (2013.01); *G16H 20/10* (2018.01); *A61M 2205/3334* (2013.01); *A61M 2205/3368* (2013.01); *A61M 2205/362* (2013.01); *A61M 2205/581* (2013.01); *A61M 2205/582* (2013.01); *A61M 2205/587* (2013.01); *A61M 2205/6054* (2013.01); *A61M 2205/8206* (2013.01); *G06F 3/02* (2013.01); *G08B 3/10* (2013.01); *G08B 5/36* (2013.01); *G08B 6/00* (2013.01)

(58) Field of Classification Search
CPC ... B67D 7/0288; G08B 214/02; A61M 11/042
USPC .............. 131/328, 329, 194, 270, 273, 361; 320/107–108, 114–115
See application file for complete search history.

(56) References Cited

U.S. PATENT DOCUMENTS

| | | | |
|---|---|---|---|
| 8,499,766 B1 * | 8/2013 | Newton | A24F 40/40 131/273 |
| 11,109,622 B1 * | 9/2021 | Woodbine | A24F 40/65 |
| 2015/0136158 A1 * | 5/2015 | Stevens | H02J 7/0091 131/329 |
| 2018/0020726 A1 * | 1/2018 | Alarcon | H05B 3/03 131/329 |
| 2019/0297952 A1 * | 10/2019 | Qiu | A24F 40/42 |
| 2020/0000143 A1 * | 1/2020 | Anderson | G06F 21/32 |

* cited by examiner

*Primary Examiner* — Tai T Nguyen
(74) *Attorney, Agent, or Firm* — Tsz Lung Yeung

(57) ABSTRACT

A vaporizer device includes an inhalation nozzle, a container containing the vaporizable material; and an atomizer arranged for carrying out a single continual atomization process for producing an inhalable vapor. A dosage reminder system for the vaporizer device includes a control module, a reminder determination unit configured for detecting a parameter during the single continual atomization process of the atomizer and a reminder element arranged for providing a reminder effect under control of the control module when the parameter reaches to a predetermined threshold.

7 Claims, 12 Drawing Sheets

A-A

VAPORIZATION DEVICE

CROSS REFERENCE OF RELATED APPLICATION

This application is a non-provisional application that claims the benefit of priority under 35U.S.C. § 120 to a provisional application, application No. 62/776,424, filed Dec. 6, 2018.

NOTICE OF COPYRIGHT

A portion of the disclosure of this patent document contains material which is subject to copyright protection. The copyright owner has no objection to any reproduction by anyone of the patent disclosure, as it appears in the United States Patent and Trademark Office patent files or records, but otherwise reserves all copyright rights whatsoever.

BACKGROUND OF THE PRESENT INVENTION

Field of Invention

The present invention relates to a vaporization device, and more particularly to a vaporization device which comprises a dosage reminder system for reminding a user to control a vapor inhalation dosage.

Description of Related Arts

A vaporization device, or a vaporizer, is used to vaporize a substance for inhalation. A typical vaporization device includes a reservoir for containing a vaporizable material which is a dry-herb, a wax, a oil or a liquid, and a heater which is arranged for being actuated to heat the vaporizable material to generate an inhalable vapor. When the vaporizable material is tobacco, the vaporization device can be an electronic cigarette that simulates the feeling of smoking without actually burning tobacco. The vaporizable material also can be a drug such as nicotine, cannabine, tetrahydrocannabinol, and DMT(N,N-Dimethltryptamine), so that the vaporization device also can serve as a drug inhalation device for medical use.

Generally, the reservoir of the vaporization device contains a volume of the vaporizable material that is able to use for a relatively long time, so that actually the user can consume as much dosage as he or she can. Thus, a problem for the use of the vaporization device is that a user is not reminded to control the dosage of the inhalable vapor. In other words, there is no suitable mechanism for restricting the inhalation dosage of the vaporizable material, resulting in that the user is prone to take an over-dosage of the inhalable vapor, and thus it may do harm to the user's health.

SUMMARY OF THE PRESENT INVENTION

The invention is advantageous in that it provides a vaporization device that introduces a dosage reminder system for reminding a user to control a dosage of vapor inhalation.

Another advantage of the invention is to provide a vaporization device, wherein the user is reminded to stop the vapor inhalation during each vaping operation so that the user is able to frequently be aware of the dosage control of the vapor inhalation.

Another advantage of the invention is to provide a vaporization device, wherein in some embodiments, the dosage reminder system can be configured to detect a time parameter such as the time duration of the atomization process in the vaping operation of the user, so as to remind the user after the user inhales the vapor for a predetermined time threshold in the vaping operation, so that the user can be reminded to stop the vapor inhalation.

Another advantage of the invention is to provide a vaporization device, wherein in some embodiments, the dosage reminder system can be configured to detect a power consumption transmitted to an atomizer during the vaping operation of the user, so as to remind the user after the power consumption reaches a predetermined power threshold in the vaping operation, so that the user can be reminded to stop the vapor inhalation.

Another advantage of the invention is to provide a vaporization device, wherein in some embodiments, the dosage reminder system can be configured to detect a temperature of the heated vaporizable material or a temperature of the inhalation vapor during the vaping operation of the user, so as to remind the user after the detected temperature reaches a predetermined temperature threshold value in the vaping operation, so that the user can be reminded to stop the vapor inhalation.

Another advantage of the invention is to provide a vaporization device, wherein in some embodiments, the dosage reminder system can be configured to detect an air flow volume during the vaping operation of the user, so as to remind the user after the detected air flow volume reaches a predetermined volume threshold value in the vaping operation, so that the user can be reminded to stop the vapor inhalation.

Another advantage of the invention is to provide a vaporization device, wherein in some embodiments, the dosage reminder system can be configured to provide a vibration alarming effect so as to remind the user to stop the vapor inhalation.

Another advantage of the invention is to provide a vaporization device, wherein in some embodiments, the dosage reminder system can be configured to provide a sound alarming effect so as to remind the user to stop the vapor inhalation.

Another advantage of the invention is to provide a vaporization device, wherein in some embodiments, the dosage reminder system can be configured to provide a lighting alarming effect so as to remind the user to stop the vapor inhalation.

Another advantage of the invention is to provide a vaporization device, wherein in some embodiments, since the dosage reminder system can be configured for reminding the user in each vaping operation, so that the user will not inhale an over-dosage of the inhalable aerosol vapor.

Another advantage of the invention is to provide a vaporization device, wherein in some embodiments, when the dosage reminder system is actuated to remind the user, the dosage reminder system can be configured to automatically stop the heating operation of the heater element, so as to stop the generation of the inhalable vapor, so that the user is prevented from overtaking the inhalable vapor.

Another advantage of the invention is to provide a vaporization device, wherein in some embodiments, after the dosage reminder system is actuated to remind the user, if the user continues to vape, the dosage remind unit can be configured to automatically stop the vapor generation operation if the time period of the vaping operation of the user reaches a predetermined amount of value, so as to prevent the over-dosage of the inhalable vapor of the user.

Another advantage of the invention is to provide a vaporization device, wherein in some embodiments, after a predetermined number of reminding operations, the dosage reminder vaporization device may be turned off, and the further vapor inhalation of the user is not available within a predetermined time period.

Another advantage of the invention is to provide a vaporization device, wherein a heating operation of the heater element can be controlled by selecting different heating modes so as to adjust the heating temperature of the vaporizable material, so that desired flavor, smell, and effects of the inhalable vapor can be provided to the user.

Another advantage of the invention is to provide a vaporization device, wherein the heating operation of the heater element can be controlled by rotating a controller knob so as to gradually adjust the heating temperature of the vaporizable material, so that the user is able to conveniently find the desired heating temperature for the vaporizable material.

Another advantage of the invention is to provide a vaporization device, wherein when the vaporizable material in a receiving cartridge is exhausted, it is easy for replacing with a new receiving cartridge.

Another advantage of the invention is to provide a dosage reminder vaporization device, wherein no complicated structure is required, and the manufacturing cost of the dosage reminder vaporization device is relatively low.

Additional advantages and features of the invention will become apparent from the description which follows, and may be realized by means of the instrumentalities and combinations particularly pointing out in the appended claims.

According to the present invention, the foregoing and other objects and advantages are attained by a vaporization device, which is capable of producing an inhalable vapor by heating a vaporizable material, comprising a vaporizer body and a dosage reminder system. The vaporizer body comprises an inhalation nozzle defining an inhalation hole, a container which contains the vaporizable material; and an atomizer arranged for carrying out at least one single continual atomization process for producing the inhalable vapor which is available for inhalation through the inhalation hole. The dosage reminder system comprises a control module, a reminder determination unit configured for detecting a parameter during each of the at least one single continual atomization process of the atomizer and a reminder element arranged for providing a reminder effect under control of the control module when the parameter reaches to a predetermined threshold.

Still further objects and advantages will become apparent from a consideration of the ensuing description and drawings.

These and other objectives, features, and advantages of the present invention will become apparent from the following detailed description, the accompanying drawings, and the appended claims.

DETAILED DESCRIPTION OF THE PREFERRED EMBODIMENT

Figure 1A:
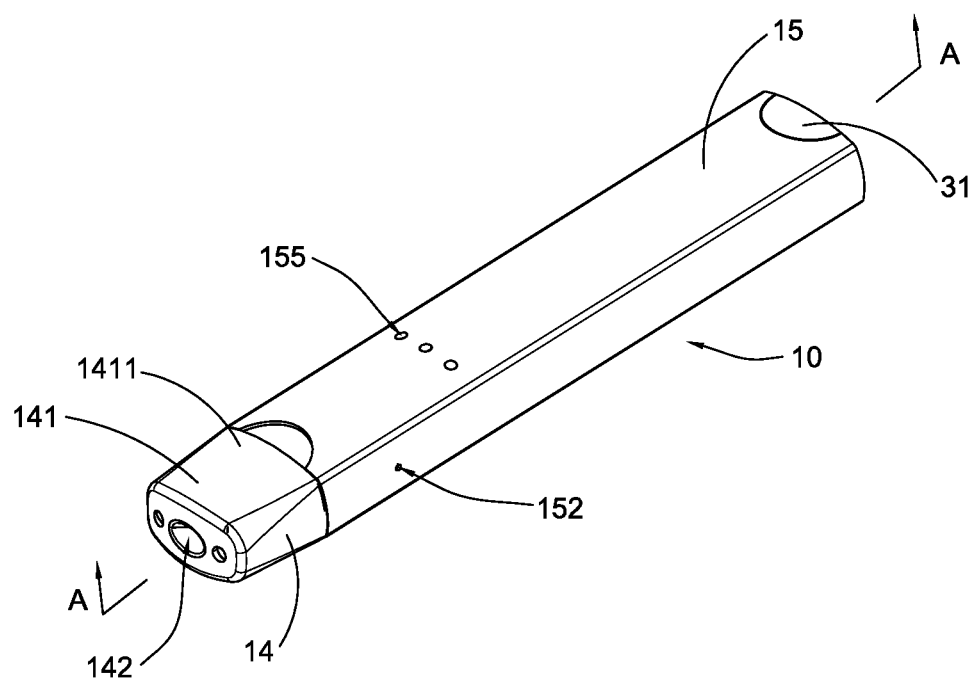
FIG. 1A is a perspective view of a vaporization device according to a preferred embodiment of the present invention.

The following description is disclosed to enable any person skilled in the art to make and use the present invention. Preferred embodiments are provided in the following description only as examples and modifications will be apparent to those skilled in the art. The general principles defined in the following description would be applied to other embodiments, alternatives, modifications, equivalents, and applications without departing from the spirit and scope of the present invention.

Those skilled in the art should understand that, in the disclosure of the present invention, terminologies of "longitudinal," "lateral," "upper," "front," "back," "left," "right," "perpendicular," "horizontal," "top," "bottom," "inner," "outer," and etc. that indicate relations of directions or positions are based on the relations of directions or positions shown in the appended drawings, which are only to facilitate descriptions of the present invention and to simplify the descriptions, rather than to indicate or imply that the referred device or element is limited to the specific direction or to be operated or configured in the specific direction. Therefore, the above-mentioned terminologies shall not be interpreted as confine to the present invention.

Referring to FIG. 1A to FIG. 5 of the drawings, a vaporization device for dosage reminding according to a preferred embodiment of the present invention is illustrated. The dosage reminder vaporization device comprises a vaporizer body 10 for generating an inhalable vapor and a dosage reminder system 20 for providing a reminding action so as to remind the user to be aware of a dosage control of the inhalable vapor and prevent the user from overtaking the inhalable vapor.

More specifically, the vaporizer body 10 comprises a container 11 which stores a vaporizable material, an atomizer 12 for being actuated to heat the vaporizable material for generating the inhalable vapor, a power source 13 for providing an electricity power supply to the atomizer 12, a inhalation nozzle 14 for the user to inhale in the inhalable vapor, and a housing 15 which defines a receiving chamber 151 for receiving the power source 13.

The dosage reminder system 20, which is powered by the power source 13, comprises a control module 21, a reminder determination unit 22, a reminder element 23 and a heating control unit 30 for controlling an operation of the atomizer 12. When the reminder determination unit 22 sends a reminding signal to the control module 21, the control module 21 generates a control command for actuating an operation of the reminder element 23.

The vaporizable material of the present invention can be dry herbs, a wax, a oil or a liquid that can be vaporized to produce the inhalable vapor containing active ingredients beneficial to the user. Accordingly, the vaporizable material can be in a solid state that can be heated to generate the inhalable vapor. The vaporizable material of this preferred embodiment is a liquid that can be heated by the atomizer 12 to produce the inhalable vapor when a temperature of the liquid approaches a boiling point of a compound in the liquid.

The vaporizable material may comprise a tobacco-based material, so that the dosage reminder vaporization device of the present invention can be embodied as an electric cigarette device. The vaporizable material may comprise a drug, and thus the dosage reminder vaporization device of the present invention can be embodied as a drug dispenser device. More specifically, the vaporizable material of the present invention may comprise one or more of botanical, nicotine, cannabinoid, tetrahydrocannabinol, DMT(N,N-Dimethltryptamine), Vitamin D, glycerin, cetirizine, fluticasone, caffeine, phenol, glycoside, terpene glycoside, alkaloid, isovaleric acid, gamma-aminobutyric acid, and *senna* glycoside. It is worth mention that the above mentioned vaporizable material of the present invention is exemplary only and not intended to be limiting, any suitable material that can be vaporized and is beneficial to the user can be used as the vaporizable material of the present invention.

The atomizer 12 of the present invention comprise a heater element 121 that can be embodied as one of a conduction heater that directly contacts the vaporizable material with an electrically heated surface, a convection heater that passing precisely heater air to the vaporizable material, and a radiant heater that uses radiant energy to provide heat. According to this preferred embodiment, the atomizer 12 of the present invention can be installed into the container 11 and is electrically connected to the power source 13 for heating the vaporizable material in the container 11 to produce the inhalable vapor in responsive to a heating control signal from the control module 21.

The power source 13 can comprise a non-rechargeable battery or a rechargeable battery. In this preferred embodiment, the power source 13 comprises a rechargeable battery 131 received in the battery chamber 151 and a charging interface 132 which is can be a USB charging interface which is provided at a bottom of the housing 15. In other alternative modes, the rechargeable battery 131 may also be wirelessly charged by a wireless charging power supply source.

Figure 2A:
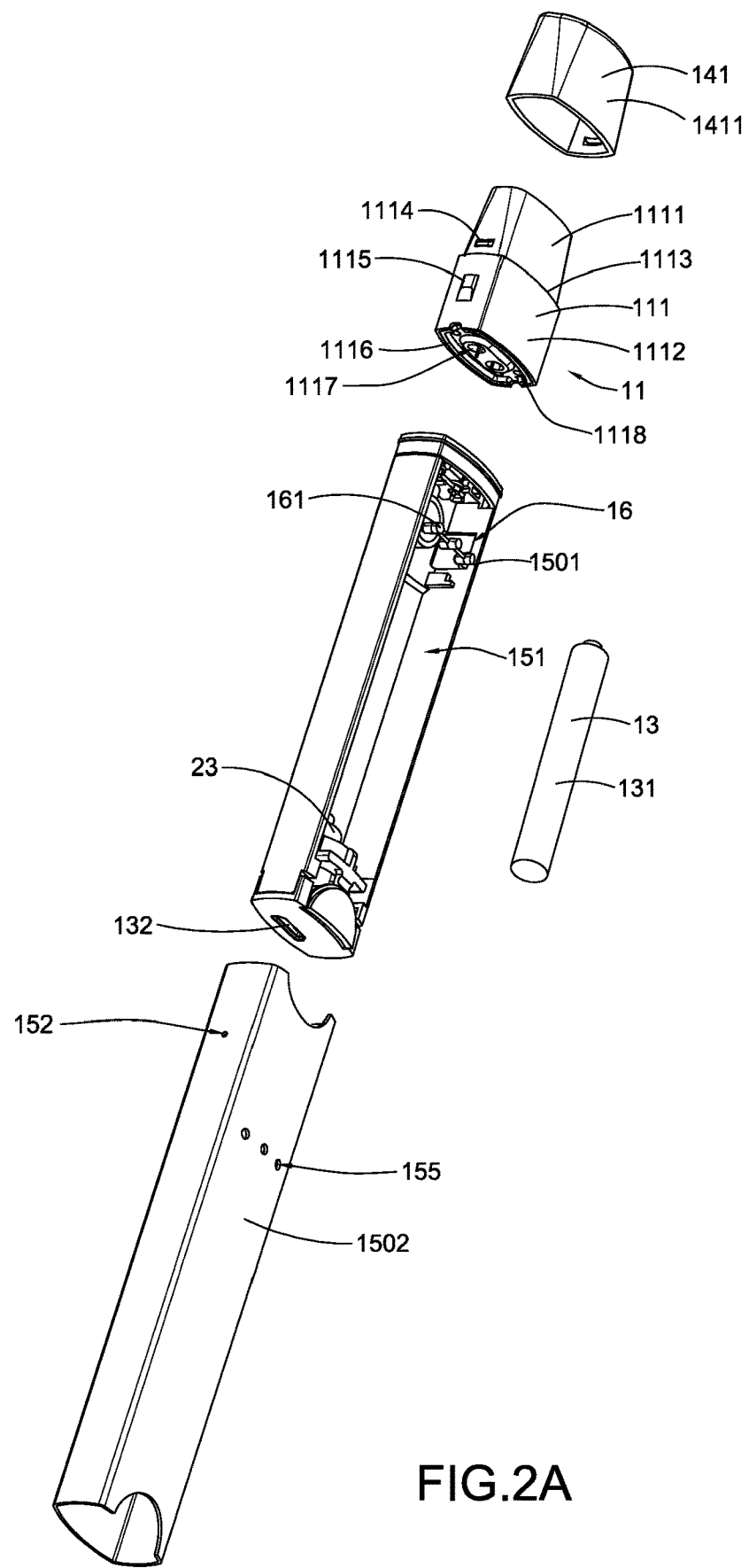
FIG. 2A is another exploded view of the vaporization device according to the above preferred embodiment of the present invention.
Figure 2B:
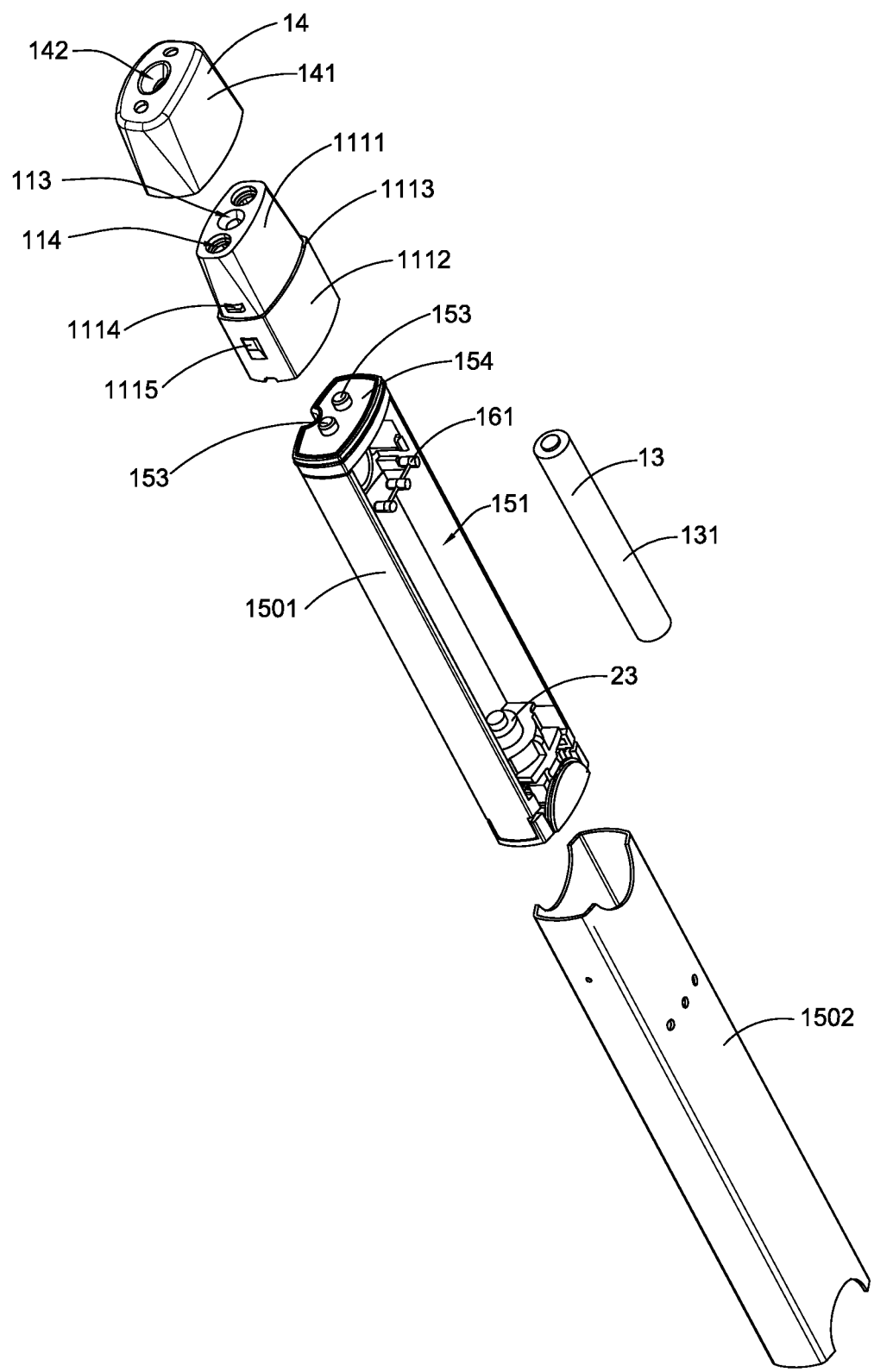
FIG. 2B is an exploded view of the vaporization device according to the above preferred embodiment of the present invention
Figure 3:
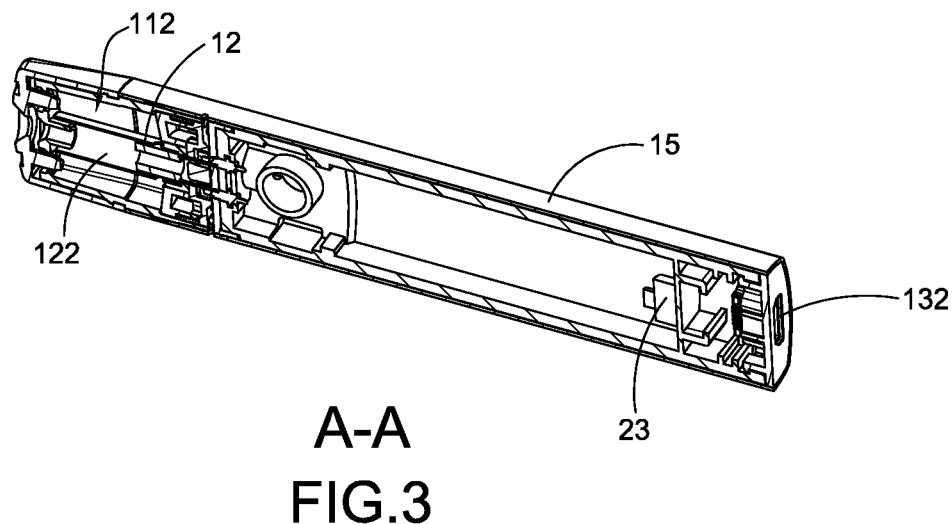
FIG. 3 is a sectional view along line A-A of FIG. 1A.

Referring to FIG. 2A to FIG. 3 of the drawings, according to this preferred embodiment, the inhalation nozzle 14 is detachably mounted with the container 11, so that the container 11 can be easy to be removed from the inhalation nozzle 14 and the housing 15 for replacing with a new container 11 containing a full amount of the vaporizable material when the vaporizable material in the old container 11 is exhausted. As an alternative mode, the inhalation nozzle 14 may be integrally formed with the container 11 to form an integral structure that is capable of being removed from the housing 15 for replacing with the new container 11.

The inhalation nozzle 14 comprises a nozzle body 141 having an inhalation hole 142, and the vaporizer body 10 may further comprise a puff sensor. When the user keeps the inhalation nozzle 14 in his or her mouth and makes a suction action, the puff sensor can detect the air flow resulted from the suction action of the user and then the control module 21 is operated to actuate the atomizer 12 for heating the vaporizable material to produce the inhalable vapor that can be inhaled by the user through the inhalation hole 142. Alternatively, the vaporizer body 10 may not be provided with the puff sensor, and a switch may be provided for being operated for actuating the atomizer 12, and when the atomizer 12 is in operation, the user is able to inhale the inhalable vapor through the inhalation hole 142.

Figure 1B:
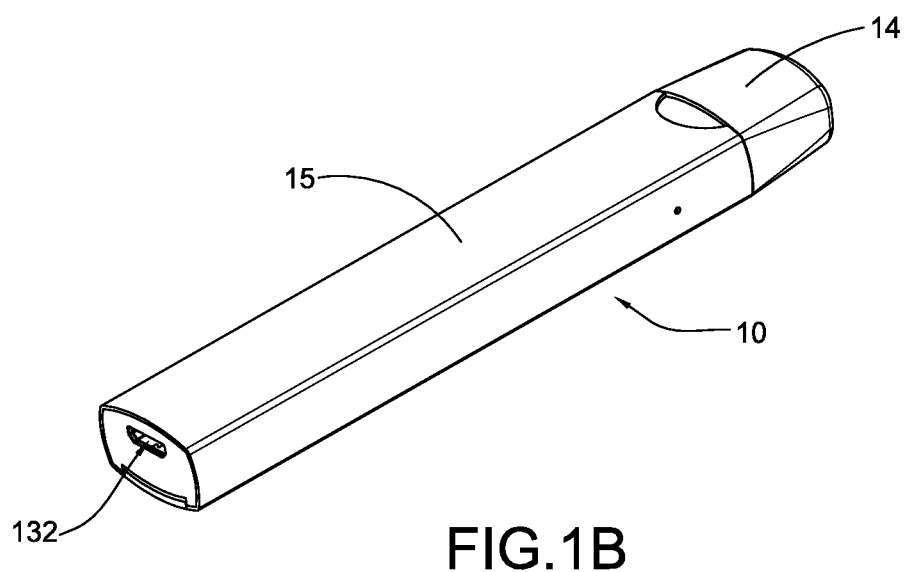
FIG. 1B is another perspective view of the vaporization device according to the above preferred embodiment of the present invention.

Accordingly, as is shown in FIG. 1A and FIG. 1B, when the inhalation nozzle 14 and the container 11 are assembled with the housing 15, the container 11 is hidden within the inhalation nozzle 14 and the housing 15. The housing 15 further has one or more communication holes 152 that air can be drawn into the housing 15 and guided to the inhalation hole 142 for enabling the air at the outside to be sucked into the dosage reminder vaporization device to create the air flow for activating the puff sensor when the user is sucking at the inhalation nozzle 14. In addition, the communication holes 152 that communicate the inside of the housing to the outside also can function as the cooling holes for discharging heat of the heater element 121 during the operation of the atomizer 12.

The inhalation nozzle 14 further comprises one or more engaging members 143, while the container 11 comprises a container body 111 defining a container chamber 112 for receiving the vaporizable material, and having a through hole 113 which is aligned with the inhalation hole 142 of the inhalation nozzle 14 and one or more engaging groove 114 each of with is detachably engaged with the corresponding engaging member 143 for detachably mounting the inhalation nozzle 14 with the container 11 so that it is easy for assembling the inhalation nozzle 14 with the container 11 and is also convenient for the user to replace a new container 11 with the inhalation nozzle 14.

The container body 111 of the container 11 has a first portion 1111 which is received and covered by the inhalation nozzle 14 and a second portion 1112 which is received and covered by the housing 15. Accordingly, as shown in FIG. 2A and FIG. 2B of the drawings, the nozzle body 141 comprises an enclosing wall 1411 which is arranged around the first portion 1111 of the container body 111 of the container 11 and the container body 111 comprises a seat wall 1113 at the top of the second portion 1112 at a joint connection between the first portion 1111 and the second portion 1112 for supporting the enclosing wall 1411 of the nozzle body 141 of the inhalation nozzle 14 when the nozzle body 141 is assembled with the container 11.

The container 11 further comprises one or more retention protrusions 1114 which are respectively protruded from an outer surface of the first portion 1111 of the container body 111 in such a manner that each of the retention protrusions 1114 is biasing against an inner surface of the enclosing wall 1411 of the nozzle body 141 of the inhalation nozzle 14 for enhancing the connection stability of the inhalation nozzle 14 and the container 11, and one or more holding protrusions 1115 which are respectively protruded from an outer surface of the second portion 1112 of the container body 111 in such a manner that each of the holding protrusions 1115 is biasing against an inner surface of the housing 15 for enhancing the connection stability between the container 11 and the housing 15, so that the container 11 is firmly assembled with the inhalation nozzle 14 and the housing 15.

In another embodiment, as is shown in FIG. 12 to FIG. 17, the inhalation nozzle 14 may be mounted to the container 11 by an integral coupling manner such as an integral welding process, the inhalation nozzle 14 further has one or more first refueling holes 144 for adding the vaporizable material, while container body 111 of the container 11 further has one or more second refueling holes 115 each of which is aligned with the corresponding first refueling holes 144 and is communicated with the container chamber 112, so that an injection portion of a refueling equipment, such as a syringe, can easily inject the vaporizable material into the container chamber 112 via the first refueling hole 144 and the corresponding second refueling hole 115, and it is easy for the vaporizable material to be filled into the container chamber 112.

Further, in this embodiment, the vaporizer body 10 comprises a barrier 17 arranged between the first refueling holes 144 and the second refueling holes 115 to prevent the vaporizable material from leaking to the mouth of the user because of the suction action. The barrier 17 is arranged to cover the second refueling holes 115 to block the connect between the first refueling holes 144 and the second refueling holes 115. The barrier 17 can be made by materials which is easy to be punctured, like silica gel, so that the injection portion of the refueling equipment can puncture the barrier 17, while the puncture will not affect the barrier 17 cover the second refueling holes 115. In addition, the barrier 17 has a channel hole 171 which is aligned with the inhalation hole 142 of the inhalation nozzle 14 and the through hole 113 of the container 11 for the inhalable vapor to be inhaled by the user through the inhalation hole 142.

Further, the in this embodiment, the vaporizer body 10 comprises an oil absorbent layer 18 for absorbing the oil contained in the inhalable vapor, so that the user will not inhale the oil and the taste of the inhalable vapor will be better. The oil absorbent layer 18 is arranged between the barrier 17 and the inhalation nozzle 14 to filtration the inhalable vapor moving from the channel hole 171 of the barrier 17 to the inhalation hole 142. Preferably, the oil absorbent layer 18 is embodied as a whole oil absorbent cotton which covers the channel hole 171 and the second refueling holes 115. Or, the oil absorbent layer 18 has one or more holes 181. One of the holes 181 is aligned with the inhalation hole 142 of the inhalation nozzle 14, and each of the other holes 181 is aligned with the corresponding first refueling hole 144.

In this embodiment, while adding the vaporizable material, the user can directly insert the injection portion of the refueling equipment into the container chamber 112 successively through the first refueling hole 144, the oil absorbent layer 18, the barrier 17 and the second refueling holes 115, rather than taking off the inhalation nozzle 14 and mounting screws. It is worth mentioning that when injecting the vaporizable material, the container 11 is inverted to be upside-down, so that when the vaporizable material is injected through an end of the container 11 having the first and second refueling holes 144 and 115, the air in the container chamber can be easy to be discharged through the connecting holes 1118.

The atomizer 12 comprises the heater element 121 having two electronic poles 1211 and a guide member 122 defining a guiding channel 1221 communicated to the through hole 113. The housing 15 further comprises an inner casing 1501 and an outer casing 1502 having the communication holes 152 at one or more of lateral sides thereof, the inner casing 1501 is coupled with the outer casing 1502 to form the receiving chamber 151 for receiving the power source 13. The housing 15 further comprises two connecting poles 153 which is protruded from a top wall 154 at a top side of the inner casing 1501 for electrically connecting with the two electronic poles 1211 respectively for electrically connecting the power source 13 with the heater element 121 of the atomizer 12.

Figure 4A:
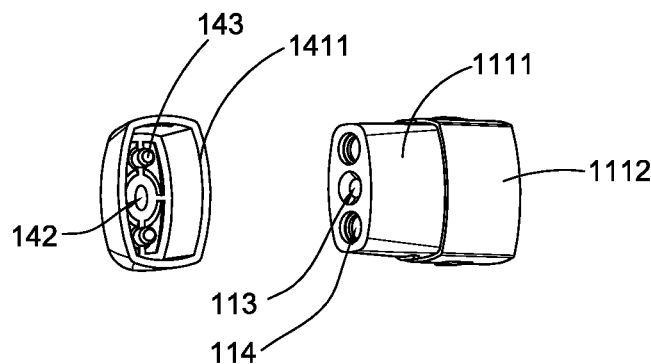
FIG. 4A is a schematic view illustrating a container and an inhalation nozzle of the vaporization device according to the above preferred embodiment of the present invention.
Figure 4B:
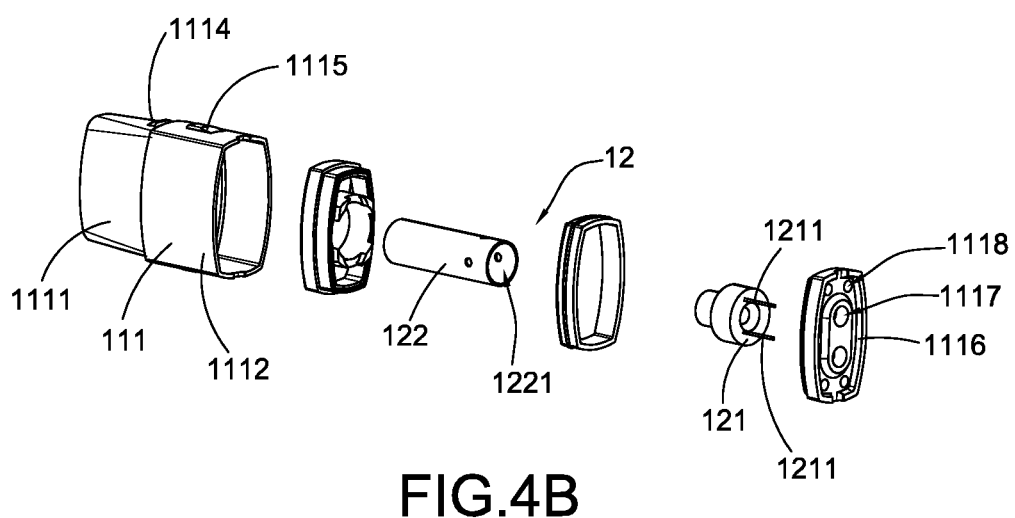
FIG. 4B is a schematic view illustrating the container and an atomizer of the vaporization device according to the above preferred embodiment of the present invention.

As is shown in FIG. 4B, the container 11 further comprises a base plate 1116 at a bottom thereof defining two penetrating holes 1117 aligning the two electronic poles 1211 with the two connecting poles 153 respectively and a plurality of connecting holes 1118. Accordingly, the air at the outside of the dosage reminder vaporization device can be inhaled into the housing 15 through the communication holes 152 and reach to the guide channel 1221 of the guide member 122 through the connecting holes 1118, so as to be mixed with the inhalable active ingredients discharged by the atomizer 12 to produce the inhalable vapor, and then is further inhaled into a mouth of the user by passing through the through hole 113 and the inhalation hole 142.

According to this preferred embodiment, the dosage reminder vaporization device further comprises a heating control unit 30 which comprises an operation switch 31 which is coupled to the control module 21, and a temperature control module 32 coupled to the control module 21. More specifically, the operation switch 31 can a button mounted to a later side of the housing 15 at a bottom portion thereof, and the button can be pressed for selecting the heating level of the heater element 121 of the atomizer 12. For instance, there are three heating modes 321 corresponding to different heating levels of the heater element 121 of the atomizer preset in the temperature control module 32, the button of the operation switch 31 can be continually clicked for two times for switching between the three heating modes 321 to control the operation of the heater element 121 of the atomizer 12.

Accordingly, the vaporizable material of the dosage reminder vaporization device contain a variety of compounds, and during the heater element 121 is in operation for heating the compounds, different compounds are gradually vaporized when the heating temperature approach the boiling points of the corresponding compounds, so that the user actually has to control a predetermined heating temperature for obtaining desired flavor, smell, and effects of the inhalable vapor. A relatively low temperature will result in thinner, smoother vapor whereas a relatively high temperature will give off massive, thick rips. In addition, the dosage reminder vaporization device may be loaded with different kinds of vaporizable material, it is actually required to test out each vaping operation on different temperatures until the user finds the ideal vaping temperature. The employment of heating control unit 30 is effective for adjusting the temperature of the vaporizable material.

It is worth mentioning that the heating control unit 30 may further comprise a preheating control module 33, and when the operation switch 31 such as the button is clicked for one time, a preheating mold of the heater element 121 of the atomizer 12 is activated under control of the preheating control module 33 for preheating the vaporizable material but the temperature of the vaporizable material does not reach the boiling point and the atomization process for producing the inhalable vapor is not started. When the time duration reaches to the predetermined time threshold, the single continual atomization process is stopped, but the preheating of the vaporizable material may be stilled in operation so as to facilitate the user to inhale in a next continual atomization process of the atomizer 12.

The vaporizer body 10 further comprises a lighting element 16 which comprises one or more lighting members 161 which are capable of providing different lighting patterns corresponding to the different heating modes 321. In other words, when clicking the button for shifting to one of the heating modes 321, the lighting members 161 is turned on for a while and provide an illumination with a predetermined pattern for the user to be easy to identify the corresponding heating mode 321.

In one embodiment, the lighting members 161 are capable of providing different lighting patterns corresponding to a power level of the power source 13. When the power source 13 comprises the non-rechargeable battery or the rechargeable battery, the lighting patterns are corresponding to a battery percent. In other words, when checking the battery percent, the lighting members 161 will light up with a predetermined pattern to indicate the corresponding battery percent. For example, all lighting members 161 being lit indicates that the battery is 70% to 100% full.

The lighting members 161 can be installed in the inner casing 1501 and the outer casing 1502 is formed with one or more exposing holes 155 which are respectively aligned with the corresponding lighting members 161 allowing light beams of the lighting members 161 to project out.

Figure 5:
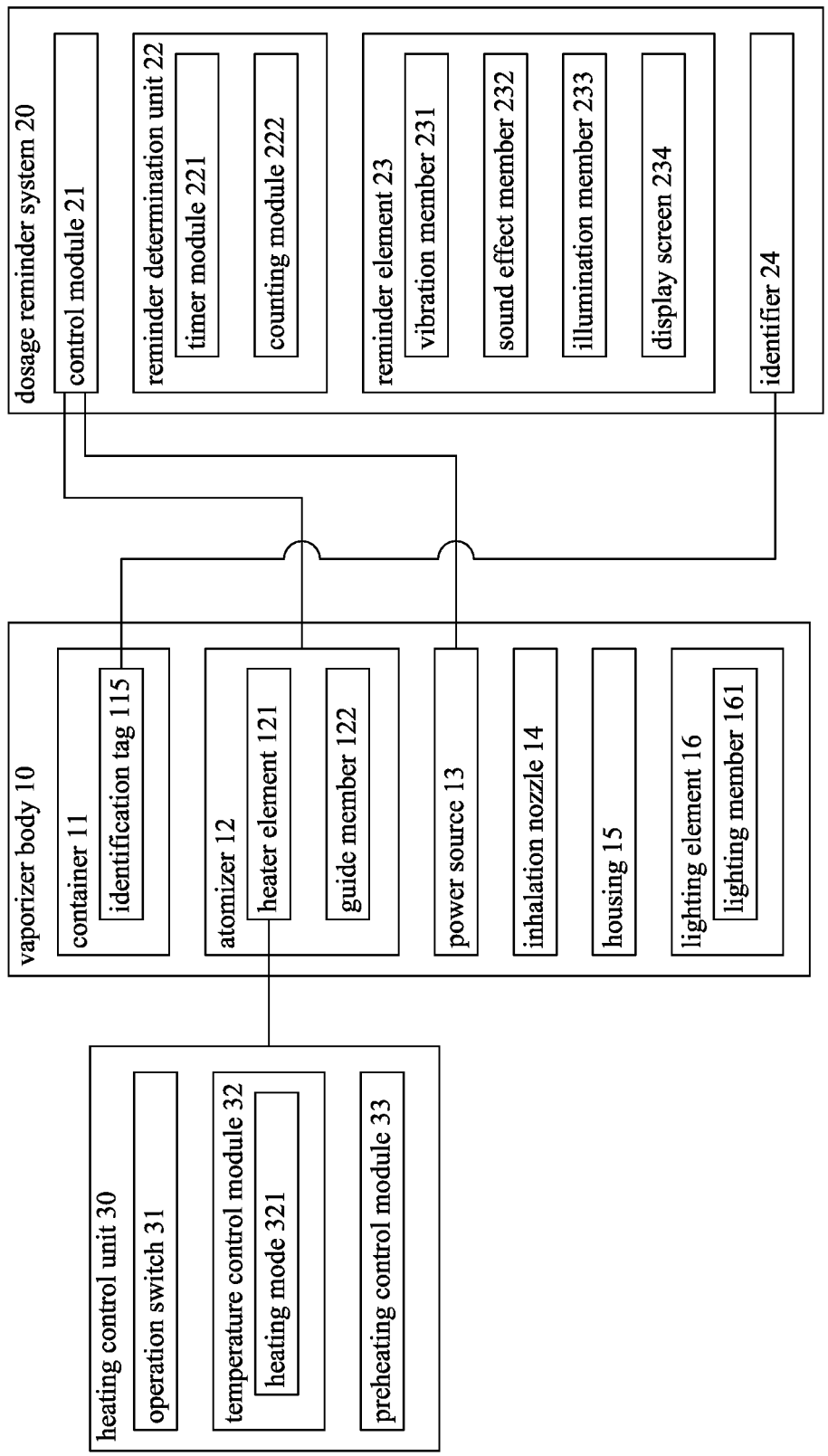
FIG. 5 is a block diagram illustrating a dosage reminder system of the vaporization device according to the above preferred embodiment of the present invention.

Referring to FIG. 5 of the drawings, according to this preferred embodiment, the reminder determination unit 22 comprises a timer module 221 coupled to the control module 21 for calculating a time duration of a single continual atomization operation of the atomizer 12. In other words, when a request signal is sent from the puff senor to the control module 21 or the request signal is generated corresponding to a button pressing action of the user for turning on an activation switch and sent to the control module 21, the control module 21 will generate an actuation command to activate the atomizer 12 for starting the atomization operation by heating the vaporizable material pumped into the atomizer 12 from the container body 111 by a pressure pump of the atomizer 12 for producing the inhalable vapor and also send a time calculating command to the timer module 221 to start to calculate the time duration of the atomization operation for producing the inhalable vapor. Accordingly, the time duration of the atomization operation can be started to count when the puff senor detects the air flow in the reminder dosage vaporization device or when the user turns on the activation switch or when the heater element 121 of the atomizer 12 begins to operate.

Accordingly, in this preferred embodiment, a predetermined time threshold is preset in the timer module 221, and when the time duration of the atomization operation reaches to the predetermined time threshold, a time reminding signal is generated and sent to the control module 21 and then the control module 21 will generate a stopping command to the atomizer 12 to stop the operation of the atomizer 12, so that the user cannot continue to inhale the inhalable vapor, the stop of the supply of the inhalable vapor can be functioned as a reminding action for reminding the user to control the dosage of the inhalable vapor.

In addition, the control module 21 of this preferred embodiment further generates a reminding actuation command to activate the reminder element 23 to produce a reminding effect. Accordingly, the reminder element 23 can be a vibration member 231 such as a vibration motor that is assembled in the housing 15 and is capable of producing a vibration effect to remind the user to be aware of the dosage control of the inhalable vapor.

The predetermined time threshold preset in the timer module 221 can be 2-10 seconds. As an example, the predetermined time threshold is 3 seconds, and when the user puts the inhalation nozzle 14 into his or her mouth and starts to inhale, the dosage reminder vaporization device begins to operate when the control module 21 is activated to actuate the atomizer 12 to heat the vaporizable material so as to produce the inhalable vapor that can be inhaled by the user. When the atomization process is continued for 3 seconds, the control module 21 receives the time reminding signal from the timer module 221 and stops the operation of the heater element 121 of the atomizer 12 and also actuates the reminder element 23 which is the vibration member 231 to produce the vibration effect to remind the user to avoid over-dosage of the inhalable vapor.

According to this preferred embodiment, during each single continual inhalation operation of the user, after the user has been inhaling the inhalable vapor for a predetermined time, the supply of the inhalable vapor is stopped and the vibration effect is produced, so that the user can be frequently reminded to control the dosage of the inhalable vapor, so that the user will not be prone to overtake the inhalable vapor, and thus it is beneficial for the health of the user.

Furthermore, after the operation of the atomizer 12 is stopped and the vibration effect is generated for a while, the user may actuate the atomizer 12 again to continue the vapor inhalation, so that the user may intermittently inhale for several times and each time is inhaled with a substantially same dosage of the inhalable vapor because each inhalation time period is determined by the predetermined time threshold preset in the timer module 221.

Actually, as a typical example, the vaporizable material contains cannabinoid which is a compound produced by marijuana, the frequently produced reminder effects change the inhaling experience of the user, the user has to stop the inhalation operation when the reminder element 23 is in operation, and thus the user is prevented from continually indulging in the inhaling process for a relatively long time.

The reminder determination unit 22 of the dosage reminder system 20 may further comprise a counting module 222 that is configured to count the number of times for the time duration reaching to the predetermined time threshold, and when the number of times is reached to a predetermined number preset in the counting module 222, a number reminding signal is sent to the control module 21, and then the control module 21 will send a force stopping command to the atomizer 12 to stop the atomizer 12 for a predetermined time period such as 24 hours during which the user is not able to activate the atomizer 12.

For example, in a specific example, the predetermined number is preset to 10 while the predetermined time threshold is 3 seconds, then the use can inhale the inhalable vapor for 3 seconds during a single continual inhalation operation and after the user has completed 10 cycles of inhalation operations, the user is prevented from inhaling the inhalable vapor within the predetermined time period.

In other words, a total time period of the atomization process also can be provided for the user by presetting the predetermined time threshold of the time duration of the atomization process and the predetermined number of times of the time durations so that the total dosage of the inhalable vapor is actually under control.

Alternatively, the counting module 222 may be configured for counting a number of actuation operations of the atomizer 12 or a number of actuation operations of the puff sensor or the activation switch. In other words, number of the operation circles of the timer module 221, the atomizer 12, the puff sensor, or activation switches can be preset so as to control the total time period available to the user.

In an alternative mode, when the time duration of the atomization operation reaches to the predetermined time threshold, a time reminding signal is generated and sent to the control module 21 and then the control module 21 sends a reminding actuation command to the reminder element 23 to actuate the reminder element 23 to produce a reminding effect such as a vibration effect to remind the user to pause the inhalation operation. At that time, the stopping command for stopping the operation of the atomizer 12 is not sent to the atomizer 12, so that the user is still able to continue to inhale the inhalable vapor with an prolonged time period, the timer module 221 starts to calculate a time duration of the prolonged time period, and when the prolonged time period has reached a certain value but the atomization process is still in operation and the user does not stop the inhalation operation, a force stopping command is sent from the control module 21 to the atomizer 12 to automatically stop the operation of the atomizer 12 so that the user is not able to continually inhale the inhalable vapor.

In addition, when the user is still allowed to continue to inhale the inhalable vapor with the prolonged time period, the timer module 221 starts to calculate the time duration of a total time period of the atomization process and when the total time period of the atomization process is reached to a predetermined value but the atomization process is still in operation, the force stopping command is sent from the control module 21 to the atomizer 12 to automatically stop the operation of the atomizer 12 so as to prevent the user from continually inhaling the inhalable vapor.

In other words, the timer module 221 of this alternative mode may be configured for calculating two time durations which are a first time duration before the reminder effect is produced and a second time duration before the atomizer 12 is forced to stop operation. When the first time duration is reached to the predetermined time threshold, the control module 21 activates the reminder element 23 to create the reminder effect such as the vibration effect, and when the second time duration which can be either the prolonged time period of the atomization process or the total time period of the atomization process is reached to a predetermined value, the control module 21 sends a force stop command to the atomizer to turn off the atomizer 12.

As a specific example, the predetermined time threshold for the first time duration can be 2 seconds while the predetermined value of the second time duration which is the total time period of the atomization process can be 3 seconds. Accordingly, when the user has inhaled for about 5 seconds, the reminder element 23 will produce a reminder effect to remind the user to be aware of the dosage control of the inhalable vapor, and when the user continues to inhale for another 3 seconds while the total time period is 5 seconds, the atomizer 12 will be forced to be turned off for preventing the user to further carry on the inhalation operation.

It is worth mentioning that when the first time duration of the atomization process is reached and the user stops the inhalation operation, the operation of the atomizer 12 can be immediately stopped under control of the control module 21.

Furthermore, as mentioned above, the reminder effect can be embodied as a vibration effect produced by the vibration member 231. Alternatively, the reminder effect can be embodied as a sound effect and the reminder element 23 is embodied as a sound effect member 232 such as a buzzer for producing the buzzing sound effect when the control module 21 activates it, or the reminder effect can be embodied as an alert lighting effect and the reminder element 23 is embodied as an illumination member 233 such as an LED illumination member for producing the alert lighting when the control module 21 activates it. Accordingly, it is worth mentioning that the lighting members 161 of the lighting element 16 also can be used as the reminder element 23 for providing the alert lighting effect.

The reminder element 23 also may be a display screen 234 mounted to the housing 15, and when the control module 21 activates the display screen, the display screen 234 is powered on to provide an illumination to produce the reminder effect. Alternatively, an alert message is displayed on the display screen 234 for reminding the user to stop the inhalation operation.

It is worth mentioning that the dosage reminder vaporization device can be shifted between a dosage control mode in which the user is reminded to control the dosage of the inhalable vapor in each single continual inhalation operation and a dosage unlimited mode in which the user can continue the inhalable vapor as long as the user wants. Accordingly, the operation switch 31 also can be operated for shifting the dosage reminder vaporization device between the two modes. For example, when the button of the operation switch 31 is continually clicked for five times, the dosage reminder vaporization device is shifted from the dosage control mode to the dosage unlimited mode, and when the button of the operation switch 31 is continually clicked for five times again, the dosage reminder vaporization device is shifted back to the dosage control mode from the dosage unlimited mode.

The container 11 may further comprise an identification tag 115 that indicates an information of the vaporizable material such as specific contents of the vaporizable material, the dosage reminder system 20 may further comprise an identifier 24 which is capable of identifying the identification tag 115. For instance, the identifier 24 can be wirelessly coupled to the identification tag 115 in a RFID identifying manner.

Accordingly, the vaporizable material can be divided into a first vaporizable material that does little harm to the health of the user and a second vaporizable material that overdosage is harmful to the user. Accordingly, when the identifier 24 recognizes that the vaporizable material is the first vaporizable material, the control module 20 will automatically operate to shift the dosage reminder vaporization device to the dosage unlimited mode that the user can continually inhale the inhalable vapor produced by the first vaporizable material and when the identifier 24 recognizes that the vaporizable material is the second vaporizable material, the control module 20 will automatically operate to shift the dosage reminder vaporization device to the dosage control mode that the user cannot continually inhale the inhalable vapor produced by the second vaporizable material, and the reminder effect is produced in each single continual inhalation operation of the user to remind the user to control the dosage of the inhalable vapor and also help the user to recognize how many dosages he or she has taken.

As an example, the first vaporizable material can be caffeine, and the user can be allowed to take a relatively large dosage of the inhalable vapor of caffeine by continuing the inhalation operation under the control of the user by himself or herself. The second vaporizable material may contain tobacco-based material, cannabinoid, or drugs, and it is preferred that the user chooses the dosage control mode to control the dosage of the inhalable vapor produced by the second vaporizable material with the help of the dosage reminder system 20.

The dosage reminder vaporization device may comprise a processor, a memory and a data storage component for achieving the above functions. Accordingly, the control module 21, the timer module 221, the counting module 22, and the temperature control module may be independent hardware components, or are all software programs which are incorporated into the processor that the processor, the memory and the data storage component are configured for implementing the control of the operation of the atomizer 12, the dosage reminding operation, and the temperature control based on different algorithms.

In one embodiment, an internal volume of the dosage reminder vaporization device is 1.0 ml. A maximum fill volume of the dosage reminder vaporization device is 1.0 ml. A weight of the empty dosage reminder vaporization device is 3.57 g to 3.59 g. A resistance of the dosage reminder vaporization device is $1.05\Omega$ to $1.35\Omega$. A diameter of a filling hole is 1.0 mm.

Accordingly, the embodiment of the present invention provides a method for indicating the dosage of the inhalable vapor produced by the atomizer 12 of the dosage reminder vaporization device as well as for reminding the user to be aware of dosage control of the inhalable vapor when vaping by the dosage reminder vaporization device, and the method comprises the following steps.

(a) In a single continual atomization process of the atomizer 12, calculate the time duration of the single continual atomization process of the atomizer 12.

(b) Activate the reminder element 23 to provide the reminder effect when the time duration of the single continual atomization process of the atomizer 12 reaches to the predetermined time threshold.

Accordingly, the time duration can be gradually counted till it amounts to the value of the predetermined time threshold. Alternatively, the step (a) can be implemented as counting down till the time period of the predetermined time threshold is elapsed. As an example, the predetermined time threshold is 3 seconds, the method can be implemented as counting from 0 to 3 seconds and then provide the reminder effect, or counting down from 3 seconds to 0 and then produce the reminder effect by the reminder element 23.

The step (b) may further comprise a step of automatically stopping the single continual atomization process of the atomizer 12 when the time duration reaches to the predetermined time threshold, so that the user is stopped from continually vaping through the dosage reminder vaporization device. The stopping of the operation of the atomizer 12 can be carried out before or after the reminder effect, or the two operations can be carried out at the same time.

In an alternative mode, after the step (b), the method may further comprise steps of: continuing the single continual atomization process of the atomizer 12, continually calculating the time duration, and automatically stopping the single continual atomization process of the atomizer 12 when the time duration reaches to the predetermined value. As mentioned above, when continually calculating the time duration, the process can be carried out as calculating the total time period of the single continual atomization process of the atomizer 12, or just recalculating the time period after the predetermined time threshold is reached.

The method may further comprise steps of counting the number of times of the time durations reaching to the predetermined time threshold in an intermittent atomization process comprising a plurality of the single continual atomization processes and force stopping the atomization process in such a manner that the atomization process is not available within the predetermined time period when the number reaches to the predetermined number. Accordingly, the number of times of the time calculation commands sent from the control module 21 to the timer module 221, or the number of time of the time reminding signals sent from the timer module 221 to the control module 21 can be used for determining the number of times of the time durations reaching to the predetermined time threshold.

Alternatively, the method may further comprise steps of counting the number of times of the actuation commands generated by the control module 21 for activating the atomizer 12, or the number of times of the stopping commands generated by the control module 21 for stopping the operation of the atomizer 12, or the number of times of the reminding actuation commands generated by the control module 21 for activating the reminder element 23 to obtain the number of times of the single continual atomization processes in an intermittent atomization process comprising the plurality of the single continual atomization processes and force stopping the atomization process in such a manner that the atomization process is not available within the predetermined time period when the number reaches to the predetermined number.

In addition, before the step (a), the method may further comprise a step of identifying the identification tag 115 on the container 11 by an identifier 24 to obtain an information of the vaporizable material for shifting the dosage reminder vaporization device to a dosage unlimited mode when the vaporizable material is the first vaporizable material and shifting the dosage reminder vaporization device to the dosage control mode when the vaporizable material is the second vaporizable material that is required for dosage control.

In other words, before the step (a), when the information of the vaporizable material in the container 11 is matched with the pre-stored information of the second vaporizable material stored in the data storage component of the dosage reminder vaporization device, the dosage reminder vaporization device is automatically shifted to the dosage control mode for carrying out the following step (a) and step (b). When the information of the vaporizable material in the container 11 is matched with the pre-stored information of the first vaporizable material stored in the data storage component of the dosage reminder vaporization device, the dosage reminder vaporization device is automatically shifted to the dosage unlimited mode, and there is no need for carrying out the following steps of (a) and (b).

Figure 6:
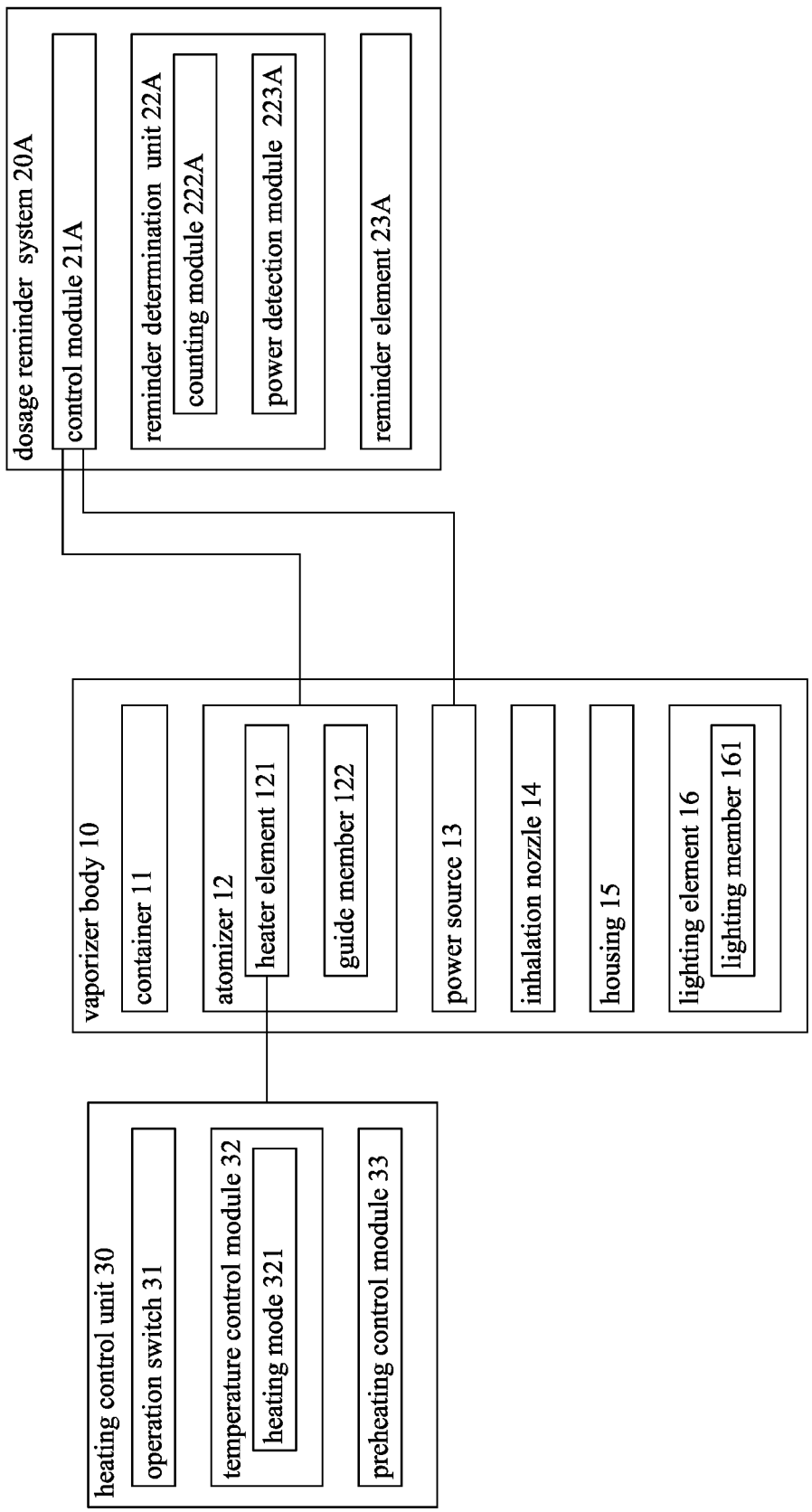
FIG. 6 is a block diagram illustrating a dosage reminder system of the vaporization device according to a first alternative mode of the above preferred embodiment of the present invention.

Referring to FIG. 6 of the drawings, a dosage reminder system 20A of the dosage reminder vaporization device according to a first alternative mode of the above preferred embodiment of the present invention. The dosage reminder system 20A of this embodiment comprises a control module 21A, a reminder determination unit 22A and a reminder element 23A for providing a reminder effect.

The reminder determination unit 22A of this embodiment comprises a power detection module 223A which is arranged for detecting a power transmitted from the power source 13 to the heater element 121 of the atomizer 12 in a single continual atomization process of the atomizer 12. When the control module 21A generates an actuation command to activate the atomizer 12 for starting the atomization operation by heating the vaporizable material pumped into the atomizer 12 for producing the inhalable vapor and also send a power detection command to the power detection module 223A to start to detect the power delivered to the atomizer 12 to carry out the atomization operation of the atomizer 12 for producing the inhalable vapor by detecting an input power of the atomizer 12 or detecting an output power of the power source 13.

Accordingly, in this preferred embodiment, a predetermined power threshold is preset in the power detection module 223A, and when the power consumption of the atomization operation reaches to the predetermined power threshold, a power reminding signal is generated and sent to the control module 21A and then the control module 21A will generate a stopping command to the atomizer 12 to stop the operation of the atomizer 12, so that the user cannot continue to inhale the inhalable vapor.

In addition, the control module 21A of this preferred embodiment further generates a reminding actuation command to activate the reminder element 23A to produce a reminding effect such as the vibration effect, the sound effect, the alert lighting effect, the alert message on the display screen, as mentioned above.

Furthermore, the user may inhale for several times. The reminder determination unit 22A of the dosage reminder system 20A may further comprise a counting module 222A that is configured to count the number of times for the power consumption of the atomizer 12 reaching to the predetermined power threshold, and when the number of times is reached to a predetermined number preset in the counting module 222A, a number reminding signal is sent to the control module 21A, and then the control module 21A will generate and send a force stopping command to the atomizer 12 to stop the atomizer 12 for a predetermined time period during which the user is not able to activate the atomizer 12. The number of the times of the power consumption of the atomizer 12 reaching to the predetermined power threshold can be obtained through the number of times of the power detection signals sent from the control module 21A to the power detection module 223A, or can be obtained through the number of times of the power reminding signals sent from the power detection module 223A to the control module 21A.

In an alternative mode, when the power consumption of the atomization operation reaches to the predetermined power threshold, a power reminding signal is generated and sent to the control module 21A and then the control module 21A generates a reminding actuation command for actuating the reminder element 23A to produce a reminding effect such as a vibration effect to remind the user to pause the inhalation operation. At that time, the stopping command for stopping the operation of the atomizer 12 is not sent to the atomizer 12, so that the user is still able to continue to inhale the inhalable vapor with an prolonged time period, the power detection module 223A starts to detect the power consumption during the prolonged time period, and when the power consumption has reached a certain value but the atomization process is still in operation and the user does not stop the inhalation operation, a force stopping command is sent from the control module 21A to the atomizer 12 to automatically stop the operation of the atomizer 12 so that the user is not able to continually inhale the inhalable vapor.

In addition, when the user is still allowed to continue to inhale the inhalable vapor with the prolonged time period, the power detection module 223A starts to detect the total power consumption of a total time period of the atomization process and when the total power consumption of the atomization process is reached to a predetermined value but the atomization process is still in operation, the force stopping command is sent from the control module 21A to the atomizer 12 to automatically stop the operation of the atomizer 12 so as to prevent the user from continually inhaling the inhalable vapor.

Accordingly, the embodiment of the present invention provides a method for indicating the dosage of the inhalable vapor produced by the atomizer 12 of the dosage reminder vaporization device as well as for reminding the user to be aware of dosage control of the inhalable vapor when vaping by the dosage reminder vaporization device, and the method comprises the following steps.

(A) In a single continual atomization process of the atomizer 12, detect the power transmitted from the power source 13 to the atomizer 12 during the single continual atomization process of the atomizer 12.

(B) When the power transmitted from the power source 13 to the atomizer 12 reaches to the predetermined power threshold, activate the reminder element 23A to provide the reminder effect.

The step (B) may further comprise a step of automatically stopping the single continual atomization process of the atomizer 12 when the power reaches to the predetermined power threshold, so that the user is stopped from continually vaping through the dosage reminder vaporization device.

In an alternative mode, after the step (B), the method may further comprise steps of: continuing the single continual atomization process of the atomizer 12, continually detecting the power transmitted from the power source 13 to the atomizer 12, and automatically stopping the single continual atomization process of the atomizer 12 when the power reaches to the predetermined value.

The method may further comprise steps of counting the number of times for the power reaching to the predetermined power threshold in an intermittent atomization process comprising a plurality of the single continual atomization processes and force stopping the atomization process in such a manner that the atomization process is not available within the predetermined time period when the number reaches to the predetermined number.

Figure 7:
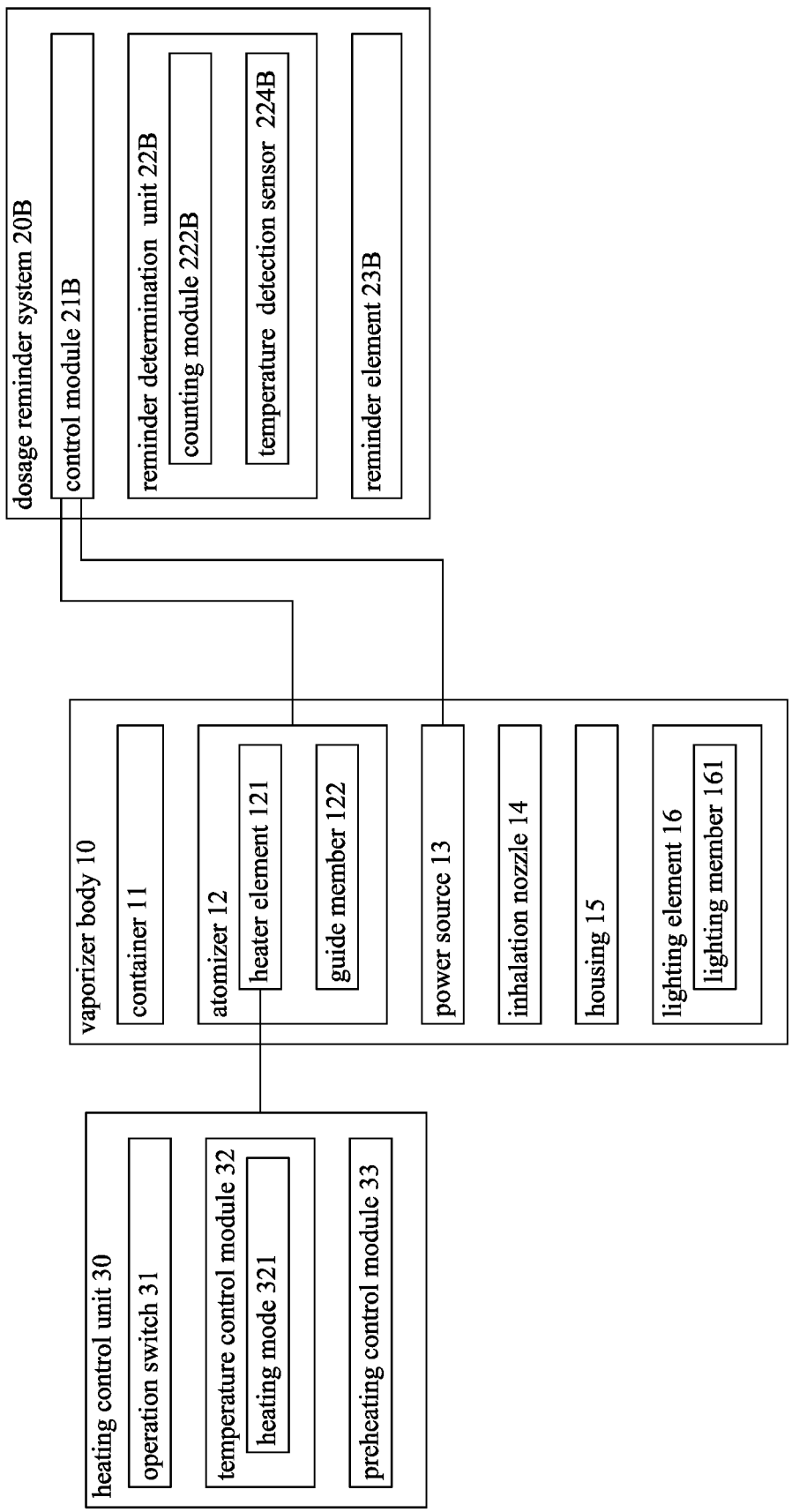
FIG. 7 is a block diagram illustrating a dosage reminder system of the vaporization device according to a second alternative mode of the above preferred embodiment of the present invention.

Referring to FIG. 7 of the drawings, a dosage reminder system 20B of the dosage reminder vaporization device according to a second alternative mode of the above preferred embodiment of the present invention. The dosage reminder system 20B of this embodiment comprises a control module 21B, a reminder determination unit 22B and a reminder element 23B for providing a reminder effect.

The reminder determination unit 22B of this embodiment comprises a temperature detection sensor 224B which is arranged for detecting a temperature of the inhalable vapor produced in a single continual atomization process of the atomizer 12 or a temperature of the heated vaporizable material. When the control module 21B generates an actuation command to activate the atomizer 12 for starting the atomization operation by heating the vaporizable material delivered into the atomizer 12 from the container body 111 for producing the inhalable vapor and also send a temperature detection command to the temperature detection sensor 224B to start to detect the temperature of the inhalable vapor produced in the single continual atomization process of the atomizer 12 or the temperature of the heated vaporizable material.

Accordingly, in this preferred embodiment, a predetermined temperature threshold is preset in the temperature detection sensor 224B, and when the detected temperature reaches to the predetermined temperature threshold, a temperature reminding signal is generated and sent to the control module 21B and then the control module 21B will generate a stopping command to the atomizer 12 to stop the operation of the atomizer 12, so that the user cannot continue to inhale the inhalable vapor.

In addition, the control module 21B of this preferred embodiment further generates a reminding actuation command to activate the reminder element 23B to produce a reminding effect such as the vibration effect, the sound effect, the alert lighting effect, the alert message on the display screen, as mentioned above.

Furthermore, the user may inhale for several times. The reminder determination unit 22B of the dosage reminder system 20B may further comprise a counting module 222B that is configured to count the number of times for the detected temperature reaching to the predetermined temperature threshold, and when the number of times is reached to a predetermined number preset in the counting module 222B, a number reminding signal is sent to the control module 21B, and then the control module 21B will generate and send a force stopping command to the atomizer 12 to stop the atomizer 12 for a predetermined time period during which the user is not able to activate the atomizer 12. The number of the times of the temperature reaching to the predetermined temperature threshold can be obtained through the number of times of the temperature detection signals sent from the control module 21B to the temperature detection sensor 224B, or can be obtained through the number of times of the temperature reminding signals sent from the temperature detection sensor 224B to the control module 21B.

In an alternative mode, when the detected temperature reaches to the predetermined temperature threshold, a temperature reminding signal is generated and sent to the control module 21B and then the control module 21B generates a reminding actuation command for actuating the reminder element 23B to produce a reminding effect such as a vibration effect to remind the user to pause the inhalation operation. At that time, the stopping command for stopping the operation of the atomizer 12 is not sent to the atomizer 12, so that the user is still able to continue to inhale the inhalable vapor with an prolonged time period, the temperature detection sensor 224B starts to detect the temperature of the inhalable vapor or the temperature of the heated vaporizable material during the prolonged time period, and when the temperature has reached a certain value but the atomization process is still in operation and the user does not stop the inhalation operation, a force stopping command is sent from the control module 21B to the atomizer 12 to automatically stop the operation of the atomizer 12 so that the user is not able to continually inhale the inhalable vapor.

Accordingly, the embodiment of the present invention provides a method for indicating the dosage of the inhalable vapor produced by the atomizer 12 of the dosage reminder vaporization device as well as for reminding the user to be aware of dosage control of the inhalable vapor when vaping by the dosage reminder vaporization device, and the method comprises the following steps.

(I) Detect the temperature of the inhalable vapor of or the temperature of the heated vaporizable material during the single continual atomization process of the atomizer 12.

(II) In responsive to the temperature reaching to the predetermined temperature threshold, activate the reminder element 23B to provide the reminder effect.

The step (II) may further comprise a step of automatically stopping the single continual atomization process of the atomizer 12 when the temperature reaches to the predetermined temperature threshold, so that the user is stopped from continually vaping through the dosage reminder vaporization device.

In an alternative mode, after the step (II), the method may further comprise steps of: continuing the single continual atomization process of the atomizer 12, continually detecting the temperature, and automatically stopping the single continual atomization process of the atomizer 12 when the temperature reaches to the predetermined value.

The method may further comprise steps of counting the number of times for the temperature reaching to the predetermined temperature threshold in an intermittent atomization process comprising a plurality of the single continual atomization processes and force stopping the atomization process in such a manner that the atomization process is not available within the predetermined time period when the number reaches to the predetermined number.

Figure 8:
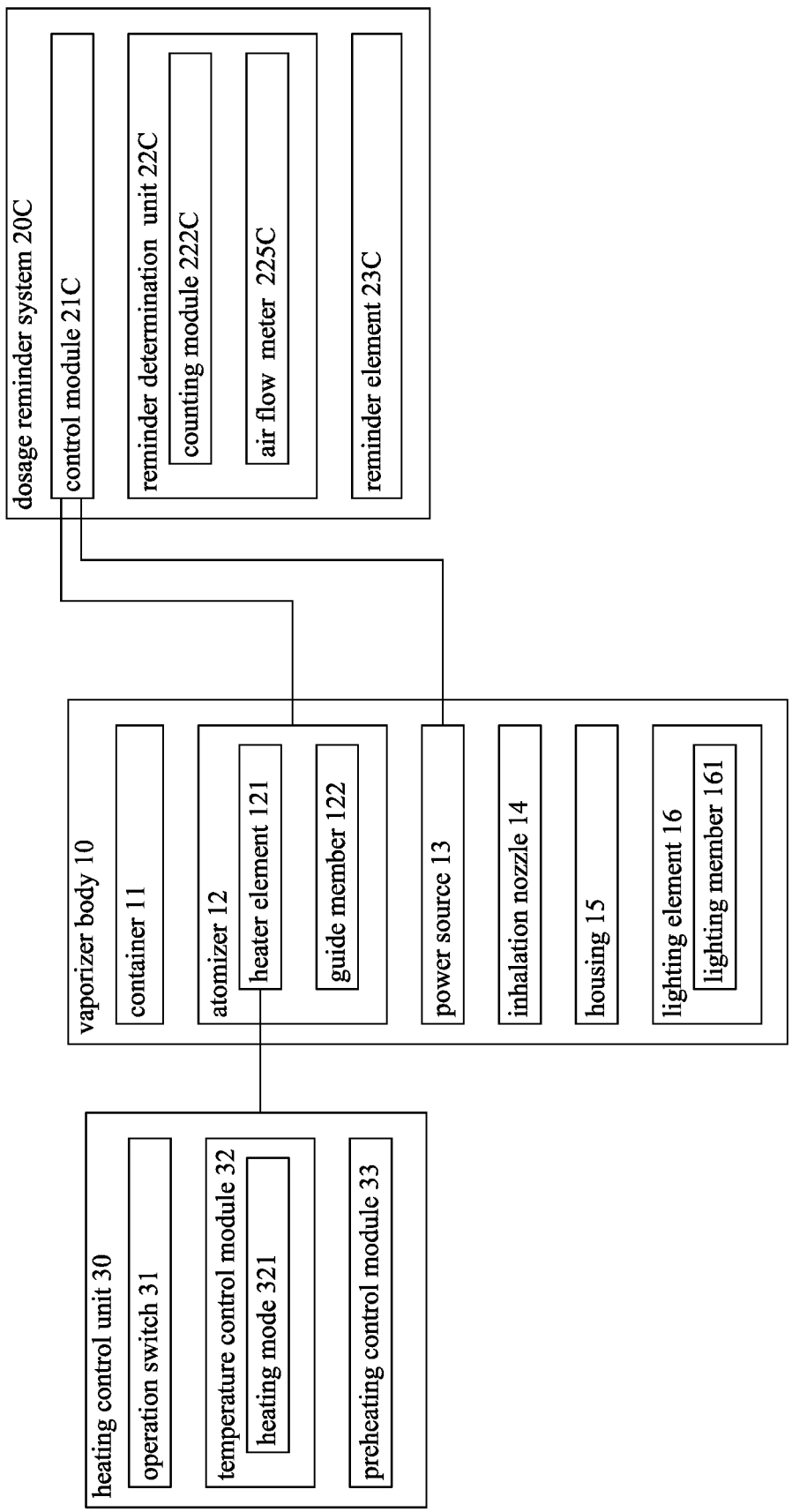
FIG. 8 is a block diagram illustrating a dosage reminder system of the vaporization device according to a third alternative mode of the above preferred embodiment of the present invention.

Referring to FIG. 8 of the drawings, a dosage reminder system 20C of the dosage reminder vaporization device according to a first alternative mode of the above preferred embodiment of the present invention. The dosage reminder system 20C of this embodiment comprises a control module 21C, a reminder determination unit 22C and a reminder element 23C for providing a reminder effect.

The reminder determination unit 22C of this embodiment comprises an air flow meter 225C which is arranged for detecting an air flow volume delivered to the user through the inhalation nozzle 14 during a single continual atomization process of the atomizer 12. Accordingly, the air flow meter 225C can be employed to achieve the function of the puff sensor mentioned above. In other words, when the air flow meter 225C detects an air flow in a flow path the dosage reminder vaporization device, the control module 21C correspondingly generates an actuation command to activate the atomizer 12 for starting the atomization operation by heating the vaporizable material pumped into the atomizer 12 from the container body 111 for producing the inhalable vapor and also the air flow meter 225C starts to meter the air flow volume transferred to the inhalation nozzle 14 for the user to inhale the inhalable vapor.

Accordingly, in this preferred embodiment, a predetermined volume threshold is preset in the air flow meter 225C, and when the air flow volume during the atomization operation reaches to the predetermined volume threshold, a volume reminding signal is generated and sent to the control module 21C and then the control module 21C will generate a stopping command to the atomizer 12 to stop the operation of the atomizer 12, so that the user cannot continue to inhale the inhalable vapor.

In addition, the control module 21C of this preferred embodiment further generates a reminding actuation command to activate the reminder element 23C to produce a reminding effect such as the vibration effect, the sound effect, the alert lighting effect, the alert message on the display screen, as mentioned above.

Furthermore, the user may inhale for several times. The reminder determination unit 22C of the dosage reminder system 20C may further comprise a counting module 222C that is configured to count the number of times for the air flow volume reaching to the predetermined volume threshold, and when the number of times is reached to a predetermined number preset in the counting module 222C, a number reminding signal is sent to the control module 21C, and then the control module 21C will generate and send a force stopping command to the atomizer 12 to stop the atomizer 12 for a predetermined time period during which the user is not able to activate the atomizer 12. As an example, the number of the times of the air flow volume reaching to the predetermined volume threshold can be obtained through the number of times of the volume reminding signals sent from the air flow meter 225C to the control module 21C.

In an alternative mode, when the air flow volume reaches to the predetermined power threshold, a volume reminding signal is generated and sent to the control module 21C and then the control module 21C generates a reminding actuation command for actuating the reminder element 23C to produce a reminding effect such as a vibration effect to remind the user to pause the inhalation operation. At that time, the stopping command for stopping the operation of the atomizer 12 is not sent to the atomizer 12, so that the user is still able to continue to inhale the inhalable vapor with an prolonged time period, the air flow meter 225C starts to continually meter the air flow volume during the prolonged time period, and when the air flow volume has reached a certain value but the atomization process is still in operation and the user does not stop the inhalation operation, a force stopping command is sent from the control module 21C to the atomizer 12 to automatically stop the operation of the atomizer 12 so that the user is not able to continually inhale the inhalable vapor.

In addition, when the user is still allowed to continue to inhale the inhalable vapor with the prolonged time period, the air flow meter 225C starts to detect the total air flow volume during the total time period of the atomization process and when the total air flow volume of the atomization process is reached to a predetermined value but the atomization process is still in operation, the force stopping command is sent from the control module 21C to the atomizer 12 to automatically stop the operation of the atomizer 12 so as to prevent the user from continually inhaling the inhalable vapor.

Accordingly, the embodiment of the present invention provides a method for indicating the dosage of the inhalable vapor produced by the atomizer 12 of the dosage reminder vaporization device as well as for reminding the user to be aware of dosage control of the inhalable vapor when vaping by the dosage reminder vaporization device, and the method comprises the following steps.

($\alpha$) Actuate the atomizer 12 to produce the inhalable vapor when the air flow in the dosage reminder vaporization is detected by the air flow meter 225C and meter the air flow volume by the air flow meter 225C during the single continual atomization process of the atomizer 12.

($\beta$) When the air flow volume reaches to the predetermined volume threshold, activate the reminder element 23C to provide the reminder effect.

The step ($\beta$) may further comprise a step of automatically stopping the single continual atomization process of the atomizer 12 when the air flow volume reaches to the predetermined volume threshold, so that the user is stopped from continually vaping through the dosage reminder vaporization device.

In an alternative mode, after the step ($\beta$), the method may further comprise steps of: continuing the single continual atomization process of the atomizer 12, continually detecting the air flow volume, and automatically stopping the single continual atomization process of the atomizer 12 when the air flow volume reaches to the predetermined value.

The method may further comprise steps of counting the number of times for the air flow volume reaching to the predetermined volume threshold in an intermittent atomization process comprising a plurality of the single continual atomization processes and force stopping the atomization process in such a manner that the atomization process is not available within the predetermined time period when the number reaches to the predetermined number.

Figure 9:
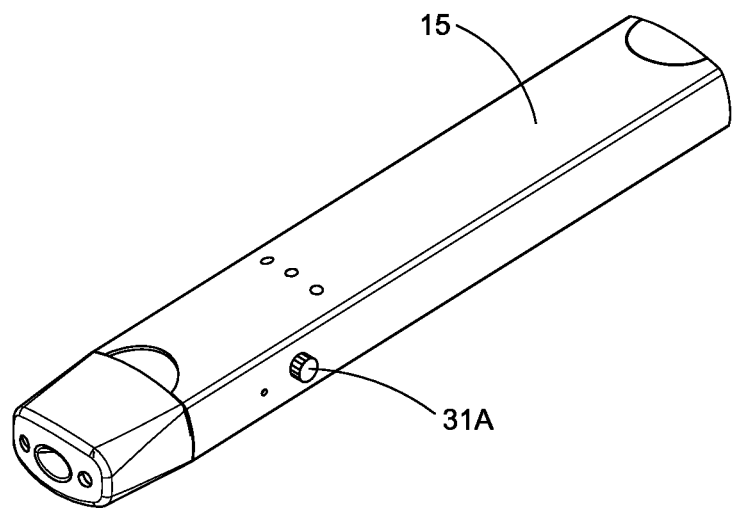
FIG. 9 is a perspective view illustrating an operation switch according to an alternative mode of the above preferred embodiment of the present invention

Referring to FIG. 9 of the drawings, a dosage reminder vaporization device according to an alternative mode of the above preferred embodiment is illustrated. According to this embodiment, the operation switch 31A is embodied as a rotation knob that is mounted to the housing 15 and can be rotated for adjusting the heating level of the heater element 121 of the atomizer 12.

Accordingly, in the above preferred embodiment, the operation switch 31 is embodied as a press button that be pressed for selecting different heating levels of the heater element 121 of the atomizer 12. The operation switch 31A of this embodiment is the rotation knob that is able to linearly adjust the heating level of the heater element 121 of the atomizer 12, so that it is more convenient for the user to find the desired heating effect for the vaporizable material, and thus desired favor and smell of the inhalable vapor can be provided to the user. In addition, it is easy for the user to identify the heating level of the heater element 121 of the atomizer through a rotation position of the rotation knob.

Figure 10:
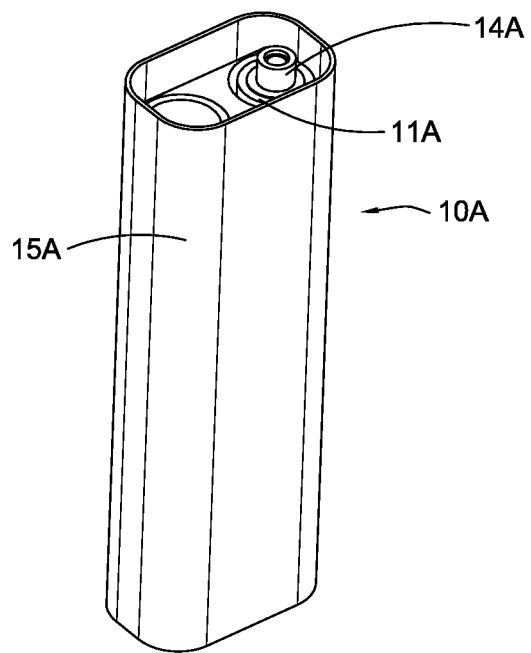
FIG. 10 is a perspective view of a vaporization device according to an alternative mode of the above preferred embodiment of the present invention.
Figure 11:
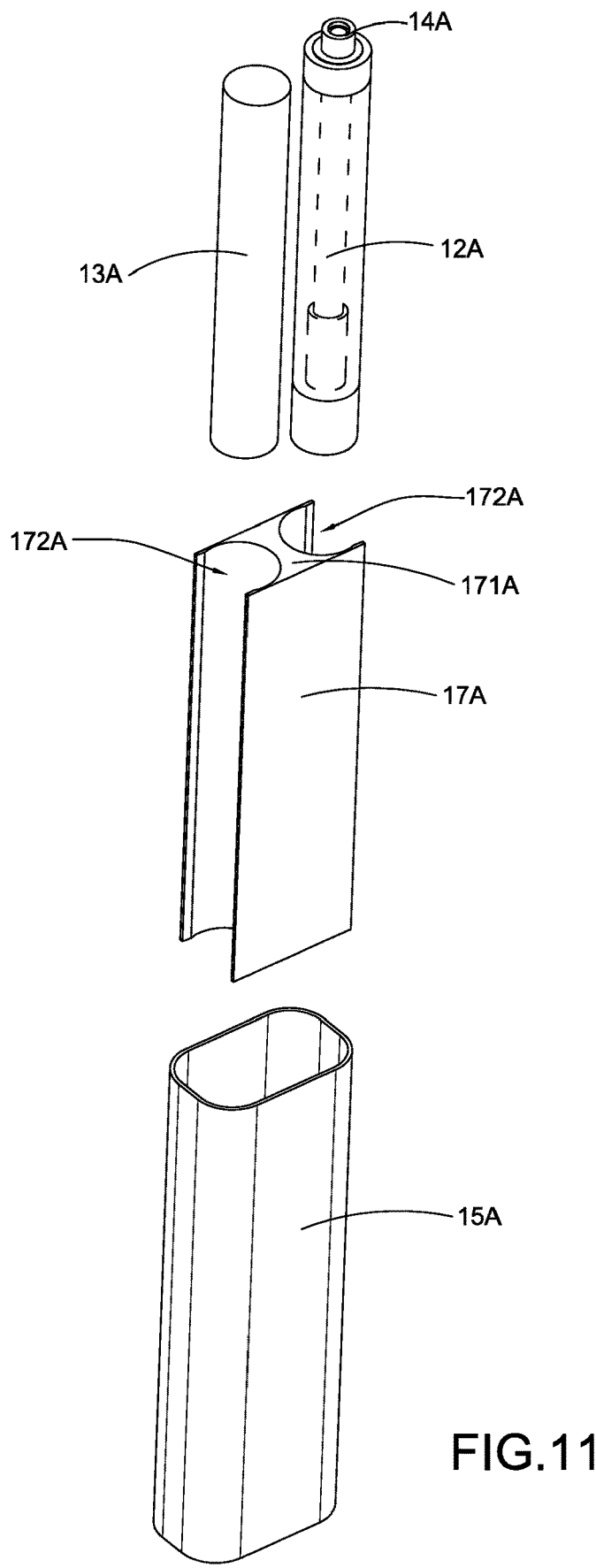
FIG. 11 is an exploded view of the vaporization device according to the alternative mode of the above preferred embodiment of the present invention.
Figure 12:
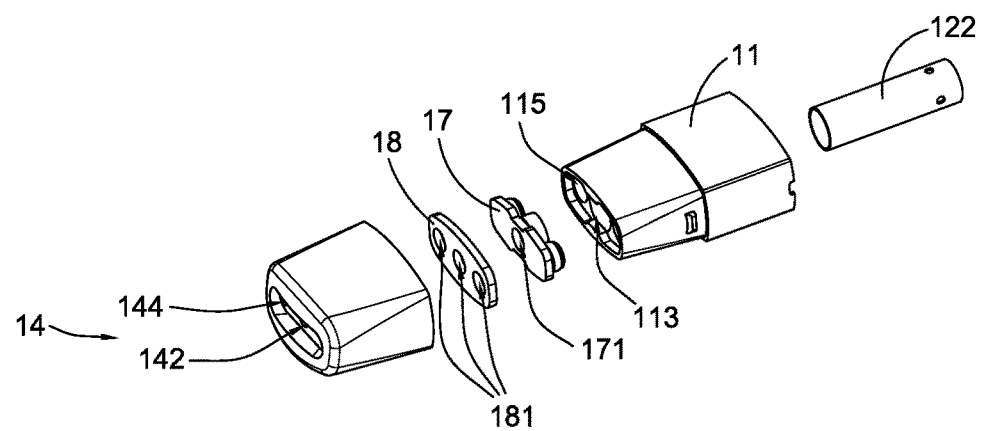
FIG. 12 is an exploded view of a container and an inhalation nozzle of a vaporization device according to the alternative mode of the above preferred embodiment of the present invention.
Figure 13:
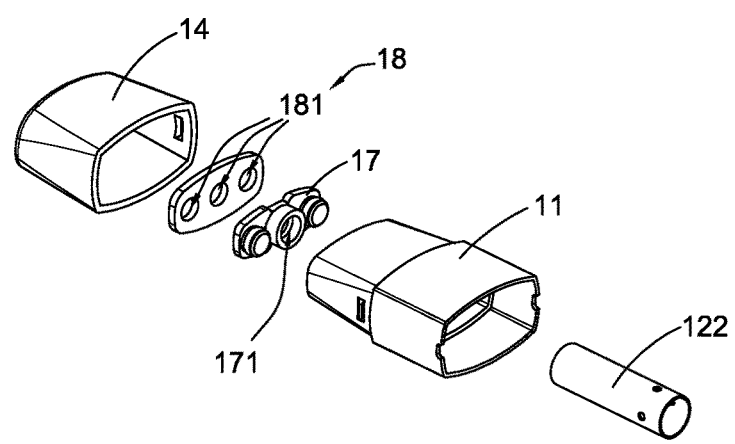
FIG. 13 is an exploded view of the container and the inhalation nozzle of the vaporization device according to the alternative mode of the above preferred embodiment of the present invention.
Figure 14:
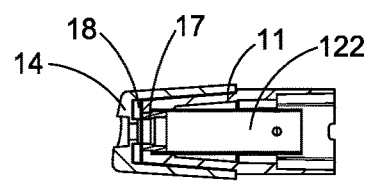
FIG. 14 is a sectional view of the container and the inhalation nozzle of the vaporization device according to the alternative mode of the above preferred embodiment of the present invention.
Figure 15:
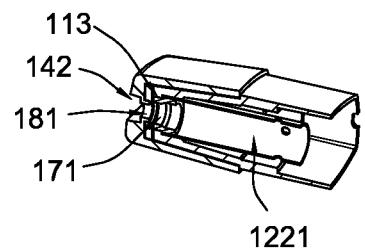
FIG. 15 is a sectional view of the container and the inhalation nozzle of the vaporization device according to the alternative mode of the above preferred embodiment of the present invention.
Figure 16:
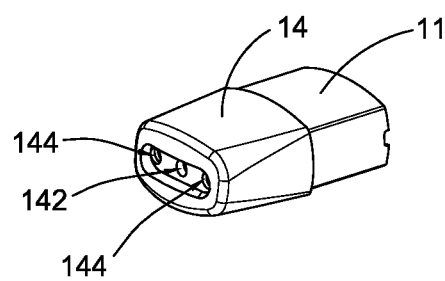
FIG. 16 is a schematic view of the container and the inhalation nozzle of the vaporization device according to the alternative mode of the above preferred embodiment of the present invention.
Figure 17:
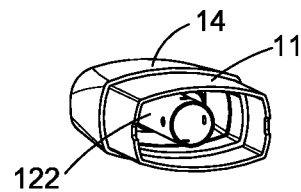
FIG. 17 is a schematic view of the container and the inhalation nozzle of the vaporization device according to the alternative mode of the above preferred embodiment of the present invention.

Referring to FIG. 10 to FIG. 11 of the drawings, a vaporization body 10A according to an alternative mode of the above preferred embodiment of the present invention is illustrated. The vaporization body 10A of this embodiment comprises a container 11A for receiving the vaporizable material, an atomizer 12A for heating the vaporizable material for producing the inhalable vapor, a power source 13A for providing the power supply to the atomizer 12A, an inhalation nozzle 14A for the user to inhale the inhalable vapor, a housing 15A for covering the container 11A, the atomizer 12A, the power source 13A, and a supporting frame 17A.

Referring to FIG. 10 and FIG. 11 of the drawings, the supporting frame 17A is employed in this embodiment for retaining the container 11A and the power source 13A in position. Accordingly, the power source 13 and the container 11 of the above preferred embodiment are arranged in an end-to-end manner that the power source 13 and the container 11 are extended in a longitudinal direction to define a length of the dosage reminder vaporization device. However, the dosage reminder vaporization device of the instant invention arranges the power source 13A and the container 11A in a side-by-side manner so as to reduce a length of the dosage reminder vaporization device.

More specifically, the supporting frame 17A comprises a frame body 171A defining two mounting grooves 172A at two opposite sides thereof for receiving the power source 13A and the container 11A respectively. As is shown in FIG. 11 of the drawings, each of the mounting grooves 172A may be formed as an indention groove and a cross section of each of the mounting grooves 172A may be in a semi-circular shape. Alternatively, each of the mounting grooves 172A also may be formed as a mounting hole which penetrates through the frame body 171A.

Accordingly, in this preferred embodiment, when the supporting frame 17A is assembled in the housing 15A, each of the mounting grooves 172A can form an assembling cavity for assembling the power source 13A and the container 11A respectively, so that the power source 13A and the container 11A are arranged side-by-side to reduce a total length of the dosage reminder vaporization device.

In addition, the container 11 of the above preferred embodiment can be a disposable container that when the container 11 is run out of the vaporizable material, a new container 11 which is filled full of the vaporizable material can be assembled into the dosage reminder device. Alternatively, the container 11A may be formed as a refillable container that there is provided with a filling hole so that new vaporizable material can be refilled into the container 11A through the filling hole so that there is no need for replacing with a new container 11A when the vaporizable material in container 11A is exhausted.

One skilled in the art will understand that the embodiment of the present invention as shown in the drawings and described above is exemplary only and not intended to be limiting.

It will thus be seen that the objects of the present invention have been fully and effectively accomplished. The embodiments have been shown and described for the purposes of illustrating the functional and structural principles of the present invention and are subject to change without departure from such principles. Therefore, this invention includes all modifications encompassed within the spirit and scope of the following claims.

What is claimed is:

1. A vaporization device for producing an inhalable vapor by heating a vaporizable material, comprising:
a vaporizer body which comprises an inhalation nozzle defining an inhalation hole;
a container which defines a container chamber for containing the vaporizable material;
an atomizer arranged for carrying out at least one single continual atomization process for producing the inhalable vapor which is available for inhalation through said inhalation hole;
a dosage reminder system which comprises a control module, a reminder determination unit configured for detecting a predetermined threshold of at least one of a time duration of said at least one single continual atomization process, a power transmitted from a power source to said atomizer and a temperature which is one of a temperature of the inhalable vapor and a temperature of a heated vaporizable material during each of said at least one single continual atomization process of said atomizer and a reminder element arranged for providing a reminder effect under control of said control module, wherein said reminder determination unit is selected from a group consisting of a timer module, a power detection module, a temperature detection sensor, and an air flow meter, where said parameter is corresponding selected from the group consisting of a time duration of each of said at least one single continual atomization process of said atomizer, a power consumption of said atomizer, a temperature of one of the inhalable vapor and the vaporizable material being heated, and an air flow volume in said dosage reminder vaporization device; and
a heating control unit which comprises an operation switch and a temperature control module coupled to said operation switch for controlling a heating level of said atomizer, wherein said operation switch is one of a button and a rotation knob, wherein said inhalation nozzle comprises a nozzle body including an encircling wall and one or more engaging member disposed within said encircling wall, wherein said container comprises a container body having a through hole aligned with said inhalation hole of said inhalation nozzle, and one or more engaging grooves detachably engaged with said one or more engaging member, wherein said dosage reminder vaporization device further comprises a power source and a housing which comprises an inner casing and an outer casing coupled with each other to define a receiving chamber for storing said power source, wherein said atomizer comprise a heater element having two electronic poles and a guider member defining a guide channel communicated to said through hole of said container body, wherein said housing further comprises two connecting poles which are detachably and electrically coupled with said two electronic poles of said heater element for electrically connecting said atomizer to said power source, wherein said container body comprises a first portion which is covered by said inhalation nozzle and a second portion which is covered by said outer casing of said housing.

2. A method for indicating a dosage of an inhalable vapor produced by an atomizer of a dosage reminder vaporization device, wherein the method comprises:
detecting a time duration of a single continual atomization process during said single continual atomization process of said atomizer;
providing a reminder effect by a reminder element when said time duration of said single continual atomization process reaches a predetermined threshold;
in said single continual atomization process of said atomizer, calculating said time duration of said single continual atomization process of said atomizer; and
activating said reminder element to provide said reminder effect when said time duration of said single continual atomization process of said atomizer reaches to a predetermined time threshold.

3. A method for indicating a dosage of an inhalable vapor produced by an atomizer of a dosage reminder vaporization device, wherein the method comprises:

detecting a power transmitted from a power source to said atomizer during a single continual atomization process of said atomizer;

providing a reminder effect by a reminder element when said power transmitted from a power source to said atomizer reaches a predetermined threshold;

in said single continual atomization process of the atomizer, detecting said power transmitted from said power source to said atomizer during said single continual atomization process of said atomizer; and activating said reminder element to provide said reminder effect when said power transmitted from said power source to said atomizer reaches to a predetermined power threshold.

4. A method for indicating a dosage of an inhalable vapor produced by an atomizer of a dosage reminder vaporization device, wherein the method comprises:

detecting a temperature which is one of a temperature of the inhalable vapor and a temperature of a heated vaporizable material during a single continual atomization process of said atomizer;

providing a reminder effect by a reminder element when one of said temperature of the inhalable vapor and said temperature of the heated vaporizable material reaches a predetermined threshold;

detecting said temperature during said single continual atomization process of the atomizer; and in responsive to said temperature reaching to a predetermined temperature threshold, activating said reminder element to provide said reminder effect.

5. A method for indicating a dosage of an inhalable vapor produced by an atomizer of a dosage reminder vaporization device, wherein the method comprises:

detecting an air flow volume in said dosage reminder vaporization device during a single continual atomization process of said atomizer;

providing a reminder effect by a reminder element when said air flow volume in said dosage reminder vaporization device reaches a predetermined volume threshold;

actuating said atomizer to produce the inhalable vapor when an air flow in said dosage reminder vaporization device is detected by an air flow meter and metering said air flow volume by said air flow meter during said single continual atomization process of said atomizer; and when said air flow volume reaches said predetermined volume threshold, activating said reminder element to provide said reminder effect.

6. A method for indicating a dosage of an inhalable vapor produced by an atomizer of a dosage reminder vaporization device, wherein the method comprises:

detecting a parameter during a single continual atomization process of said atomizer;

providing a reminder effect by a reminder element when one of a time duration of said single continual atomization process, a power transmitted from a power source to said atomizer, a temperature which is one of a temperature of the inhalable vapor and a temperature of a heated vaporizable material, and an air flow volume in said dosage reminder vaporization device reaches a predetermined threshold;

in an intermittent atomization process comprising a plurality of said single continual atomization processes of said atomizer, producing said reminder effect by said reminder element in each of said single continual atomization processes of said atomizer;

counting a number of times of said parameter reaching to said predetermined threshold in said intermittent atomization process comprising the plurality of said single continual atomization processes; and force stopping an operation of said atomizer in such a manner that said operation of said atomizer is not available within a predetermined time period when said number reaches to a predetermined number.

7. A method for indicating a dosage of an inhalable vapor produced by an atomizer of a dosage reminder vaporization device, wherein the method comprises:

detecting a parameter during a single continual atomization process of said atomizer, wherein said parameter is selected from a group consisting of a time duration of said single continual atomization process, a power transmitted from a power source to said atomizer, a temperature which is one of a temperature of the inhalable vapor and a temperature of a heated vaporizable material, and an air flow volume in said dosage reminder vaporization device;

providing a reminder effect by a reminder element when said parameter reaches a predetermined threshold;

continuing said single continual atomization process of said atomizer;

continually detecting said parameter; and automatically stopping said single continual atomization process of said atomizer when said parameter reaches to a predetermined value.

\* \* \* \* \*